(12) United States Patent
Coghlan et al.

(10) Patent No.: US 6,265,156 B1
(45) Date of Patent: *Jul. 24, 2001

(54) HYBRIDIZATION HISTOCHEMISTRY METHOD FOR DETERMINING THE PRESENCE AND LOCATION IN ANIMAL OR PLANT TISSUE OF RNA

(75) Inventors: John P. Coghlan, Kew; Jennifer D. Penschow, Greensborough; Geoffrey W. Tregear, Hawthorn; Hugh D. Niall, Elwood, all of (AU)

(73) Assignee: Howard Florey Institute of Experimental Physiology and Medicine, Victoria (AU)

(*) Notice: Subject to any disclaimer, the term of this patent is extended or adjusted under 35 U.S.C. 154(b) by 0 days.

This patent is subject to a terminal disclaimer.

(21) Appl. No.: 08/889,065

(22) Filed: Jul. 7, 1997

Related U.S. Application Data

(62) Continuation of application No. 08/723,535, filed on Sep. 30, 1996, now abandoned, which is a continuation of application No. 08/459,498, filed on Jun. 2, 1995, now abandoned, which is a continuation of application No. 07/294,971, filed on Dec. 30, 1988, now Pat. No. 5,597,692, which is a continuation of application No. 06/815,095, filed as application No. PCT/AU85/00070 on Apr. 4, 1985, now abandoned.

(30) Foreign Application Priority Data

Apr. 5, 1984 (AU) .................................................. 4433/84

(51) Int. Cl.⁷ ........................................................ C12Q 1/68
(52) U.S. Cl. ........................... 435/6; 436/501; 536/25.3
(58) Field of Search ................... 435/6, 810; 436/501; 536/23.1, 24.1, 25.3, 24.3–24.33; 935/77, 78

(56) References Cited

U.S. PATENT DOCUMENTS 4,401,759   8/1983   Rubin et al. ............................. 435/91
5,597,692 * 1/1997   Coghlan et al. ......................... 435/6

OTHER PUBLICATIONS

Angeren et al. (1981) Nucleic Acids Res., vol. 9, No. 21, pp. 2819–2840.*
Cox et al. (1984) Developmental Biology, vol. 101, pp. 485–502.*
Hudson et al, *Endocrinology*, 108(1):353–356 (1981).
Szostak et al, *Methods in Enzynol.*, 68:419–428 (1979).
Suggs et al, *Proc. Natl. Acad. Sci.*, 78:6613–6617 (1981).
Singer et al, *Proc. Natl. Acad. Sci.*, 79:7331–7335 (1982).
Szostak et al, *Nature*, 265:61–63 (1977).
Ruth et al, *DNA*, 3:173 (1984).
Chollet et al, *Nucleic Acid Res.*, 13:1529 (1985).
Kempe et al, *Nucleic Acid Res.*, 13:45 (1985).
Murasugi et al, *DNA*, 3:269 (1984).
McConaughy et al, *Biochem. Biophys. ACTA*, 149:180 (1967).
Tecott et al, "In Situ Hybridization: Application to Neurobiology", Oxford University Press, pp. 3–24 (1987).

\* cited by examiner

*Primary Examiner*—Ardin H. Marschel
(74) *Attorney, Agent, or Firm*—Sughrue, Mion, Zinn, Macpeak & Seas, PLLC

(57) ABSTRACT

A method for determining the presence and location in animal or plant tissue of a specific polynucleotide population comprising: (a) preparing a section of the tissue to be examined; (b) contacting the tissue section under hybridization conditions with a synthetic, labelled oligonucleotide probe which is complementary to a representative portion of the target polynucleotide; (c) removing unhybridized probe material from the tissue section; and (d) detecting or identifying the locations in the tissue section where labelling or hybridization of the labelled probe has occurred. A diagnostic kit for use in performance of the above method is also disclosed.

5 Claims, 4 Drawing Sheets

HYBRIDIZATION HISTOCHEMISTRY METHOD FOR DETERMINING THE PRESENCE AND LOCATION IN ANIMAL OR PLANT TISSUE OF RNA

This is a Continuation Application of Ser. No. 08/723,535, file Sep. 30, 1996 (now abandoned); which in turn is a Continuation Application of Ser. No. 08/459,498, filed Jun. 2, 1995 (now abandoned); which in turn is a Continuation Application of Ser. No. 07/294,971, filed Dec. 30, 1988 (now U.S. Pat. No. 5,597,692); which in turn is a Continuation Application of Ser. No. 06/815,095, filed Dec. 4, 1985 (now abandoned) which is a 371 filing of PCT/AU85/00070 Apr. 4, 1985.

This invention is concerned with improvements in and relating to hybridization histochemistry. The invention is particularly concerned with, although not limited to, improved techniques for the application of hybridization histochemistry in medical diagnosis and research.

The procedure of in situ hybridization, termed "hybridization histochemistry", has been developed to locate in specially prepared whole sections of tissue those areas which contain specific mamqA populations, the presence of which would indicate that a certain gene is "switched on", and production of a specific protein or peptide is, therefore, highly probable.

Hybridization between complementary strands of nucleic acids has become one of the powerful tools of molecular biology. The method stems from the fact that two complementary strands in a DNA double helix or a DNA/RNA duplex can be separated by denaturation and then reannealed (hybridized) back together under conditions where the hydrogen bonding of base pairs is favoured. One of the most exploited applications of hybridization technique has been in situ procedures where one of the annealing strands has been immobilized. Much of this work is based on the use of nitrocellulose to immobilize the DNA. Often the complementary labelled strand is added as soluble, radioactively-labelled probe which after hybridization and removal of the unbound probe, can be localized and semi-quantitated by autoradiography.

We have recently shown that these procedures can be applied to sections of tissue, by the treatment of cells or tissue sections so as to immobilize and protect naturally occurring DNA or RNA for in situ tissue hybridization while at the same time retaining sufficient cellular morphology for accurate histological location. These in situ hybridization techniques, which use radiolabeled cloned cDNAs, have been successfully employed to localize endorphin, GH, relaxin, and calcitonin mRNAs in fixed tissue slices. (See: Hudson, P., Penschow, J., Shine, J., Pyan, G., Niall, H. and Coghlan, J. Hybridization Histochemistry: Use of recombinant DNA as a "homing probe" for tissue localization of specific mRNA populations. *Endocrinology*, 1981, 108: 353–356. Jacobs, J., Simpson, E., Penschow, J. P., Hudson, P., Coghlan, J. and Niall, H. Characterization and location of calcitonin mPNA in rat thyroid. *Endocrinology*, 1983, 113: 1616–1622).

The basis of this technique is the incubation of a radioactively-labelled recombinant cDNA probe with a carefully prepared section of tissue. After appropriate washing the tissue is dried and autoradiography is used to identify specific cell populations or tissue regions binding the probe. The principle is thus similar to the widely used immuno-histochemical procedures based upon binding of fluorescent, radioactive or peroxidase labelled antibodies.

The cDNA probe is obtained by standard cloning techniques to obtain a double-stranded copy of the target mRNA. The double-stranded copy is denatured to produce single-stranded cDNA from which labelled copy probe is made.

It was surprising that this approach has not, to our knowledge, been previously established because recombinant cDNA probes have been available for several years. There are a number of published studies which used partially purified rather than recombinant cDNA probes. This is an important distinction because recombinant probes with their absolute homogeneity guaranteed through the cloning procedure used to produce them, provide a degree of specificity of labelling which cannot be matched by any partially purified probe enriched for a particular molecular species. More recently there have been other reports on the use of cDNA probes either radioactively labelled or using fluorescent, enzymic or other labels of the hybridization sites.

Our previous work has shown clearly that it is possible where a DNA probe is available to identify which tissues secrete a particular protein. Biological applications of the techniques seem to be limited only by the specificity and type of probe which is available.

Until recently most of the work on hybridization histochemistry has been concerned with the use of probes of recombinant cDNA derived from natural mRNA or DNA. This has limited the application of the technique to cases where the natural RNA or DNA was available, e.g., had been or could be cloned from a natural source. This has naturally limited the scope of the method, as in many potential areas of application, the required RNA or DNA was not available and/or its structure was unknown.

The present invention is based on the substitution of synthetic oligonucleotide probes for cDNA obtained from or via natural sources. We have found that comparatively short probes, from about 10 to 100 nucleotides, preferably about 20 to 40 nucleotides, are usually of sufficiently unique structure to provide the necessary selectivity.

The synthesis of oligonucleotide sequences containing up to about 100 nucleotides is now readily achieved using known equipment and techniques.

Furthermore, in cases where the nucleotide sequence is not known but where information on the structure of a peptide or protein is available, it is now possible to predict with considerable certainty the DNA or RNA sequence which codes for that peptide or protein. Computer programs now available enable the redundancies in the genetic code to be resolved by predicting the most probable nucleotide sequence (for any given species) where any ambiguity exists.

Thus once the structure of a particular peptide or protein is known or can be inferred with reasonable certainty, the corresponding mRNA structure can be predicted, and a matching or complementary oligonucleotide probe can then be constructed and used to search for the natural mRNA population by the technique of hybridization histochemistry.

It is usually not necessary to know the complete amino acid sequence as useful oligonucleotide probes may be constructed from partial sequences of as few as 7 to 10 amino acids.

This approach can be used to confirm and extend studies indicating that many peptide or protein hormones are made in multiple sites (brain, gut, placenta). Biosynthesis can be distinguished from storage, and estimates of mRNA turnover made. Moreover, within a heterogeneous individual tissue (whether normal or neoplastic) it is possible to identify which cell types make a particular known product. With further increases in resolution, it should be possible to study the subcellular localization of mRNA. Probes complementary to certain non-coding regions of chromosomal DNA (e.g. to intervening sequences) might also enable studies of the location of the initial mRNA transcript (pre mRNA) and the fate of the excised segments. Specific cDNA probes can be used to detect either viral RNA/DNA or virus-specific mRNA in infected tissues. This technique could be particularly useful when a particular virus is difficult to grow in culture. This new approach to hybridization histochemistry will also prove especially useful in clinical diagnosis.

The general approach described above can also provide a method for detecting mRNA species or DNA in plant cells and tissues, in particular the detection of the state of activity of specific plant genes and the detection of plant pathogens such as, for example, plant viruses, fungi and viroids responsible for plant diseases of economic importance.

According to one aspect of the present invention there is provided a method for determining the presence and location in animal or plant tissue of a specific polynucleotide population which comprises:

(a) preparing a section of the tissue to be examined;
(b) contacting the tissue section under hybridization conditions with a synthetic, labelled oligonucleotide probe which is complementary to a representative portion of the target polynucleotide;
(c) removing unhybridized probe material from the tissue section; and
(d) detecting or identifying the locations in the tissue section where labelling by hybridization of the labelled probe has occurred.

Synthesis of oligonucleotide probes may be carried out by any of the known procedures including solution, solid-phase, enzymic and combinations thereof, and particularly methods involving DNA polymerase-mediated "repair synthesis" of synthetic oligonucleotide substrates having short stretches of complementary sequence at their 3' termini. In the presence of DNA polymerase and the four deoxyribonucleotide triphosphates (which may be appropriately labelled) these primer-templates are converted to full-length double stranded DNA's from which the single stranded probe may be obtained. (See for example, Rossi, J. J., Kierzek, R., Huang, T., Walker, P. A. and Itakura, K., J. Biol. Chem. 257, 9226–9229, 1982.)

As indicated above, the usual method of probe labelling in the past has been to use radioactive labelling, especially with 3 P, and to carry out step (d) by the normal procedures of autoradiography. While this type of labelling can be used in the method of the present invention, it may be complex and time consuming, as well as requiring access to, and facilities for the handling and disposal of the necessary radioisotopes. This may be disadvantageous in some circumstances, such as in routine clinical diagnostics.

In an alternative embodiment of the Invention therefore, non-radioactive labelling is employed, such as, for example, fluorescent or enzymic labels, which are known per se in the immunohistochemical art, and to thus carry out step (d) by the appropriate standard procedures for development and/or identification of such labels.

In another embodiment, a non-radioactive label which may comprise or include a specific molecule or atom capable of detection by its spectral or other properties may be attached to the synthetic probe.

As already suggested, the method of the invention has particular application in the field of clinical diagnosis and for this purpose it is desirable to make the method available to technical staff who do not have special expertise in the techniques of hybridization histochemistry.

Therefore according to a further aspect of the invention, there is provided a diagnostic kit for use in performing the invention, which comprises a labelled synthetic oligonucleotide probe as specified above.

Because the method of the invention involves special preparation of the tissue samples, the diagnostic kit in its preferred form includes the reagents required for tissue section preparation, and, where necessary, reagents for the detection of the labelled sites after hybridization, as well as instructions for carrying out the method.

The advantages which are achieved by using synthetic oligonucleotide probes in hybridization histochemistry, in accordance with this invention, include the following:

Convenience—Synthetic oligonucleotide probes are readily acquired without the need to isolate and clone natural polynucleotides.

Adaptability—Synthetic oligonucleotide probes can be precisely "tailored" to the appropriate length for any desired level of hybridization specificity. Very long or very short probes may be too non-specific. Variations in nucleotide sequences are readily obtained. Furthermore, specific synthetic probes may be "tailored" so as to correspond to regions of maximum difference between two or more substantially similar nucleotide sequences.

Availability—As well as allowing an infinite variety of probes to be produced, the synthetic approach also allows larger amounts of the probes to be produced than could be achieved reasonably by cloning.

Consistency and flexibility—Labelling is readily controlled during synthesis to provide any required extent and positioning, thus providing a greater degree of consistency and reliability.

Effectiveness—The close control of probe design which is possible can provide better definition, i.e., clearer "pictures" than can be obtained with "natural" probes. For example, cloned cDNA probes are often contaminated by bacterial DNA which is difficult to remove. Furthermore, cDNA probes obtained from *E. coli* plasmids are not particularly effective for the localization of proteins in gastrointestinal or infected tissue because of high background interference. Non-specific labelling can also arise because of the presence of poly A tails in cloned sequences which often can not be deleted because of the lack of appropriate endonuclease cleavage sites.

The method of the invention is further illustrated by the following discussion, which illustrates the basic techniques involved, and specific examples of the method.

Preparation of Oligonucleotide Probes

Figure 1A:
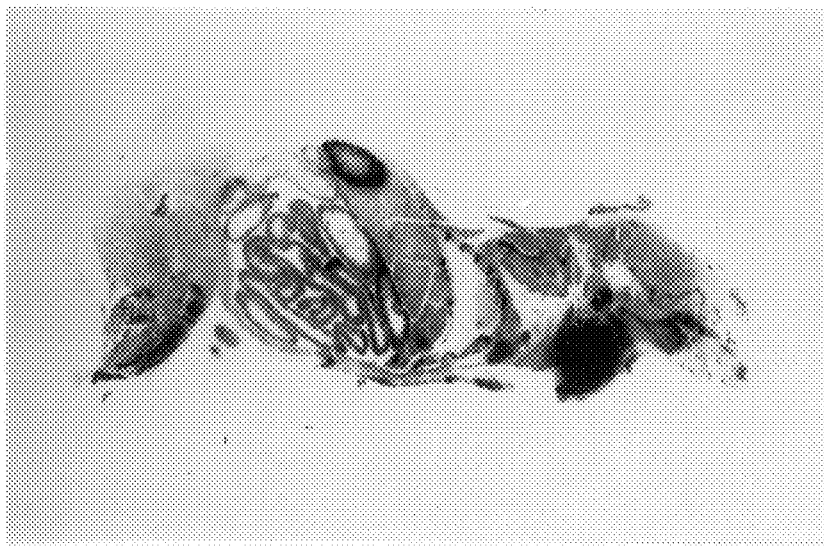
FIG. 1A is an X-ray film autoradiograph from a 40 µm section of a whole male Swiss mouse showing mRNA for kallikrein in kidney cortex and salivary glands (Mag.×2).

The most efficient of the currently available methods for the synthesis of oligodeoxyribonucleotides is the solid-phase phosphoramidite method (Caruthers et al., Cold Spring Harbour Symp. Quant. Biol. 47, 411–418 (1982), Adams et al, J. Am. Chem. Soc. 105, 661 (1983)). In this procedure, the solid phase is long alkyl chain controlled pore glass (Adams et al., supra) (CPG), a porous matrix with a pore size of 500A, and particle size of 115–117 μm. This support has greater mechanical strength than silica and gives faster couplings and higher yields. The first nucleoside is attached to the solid support through its hydroxyl group by an ester linkage to a succinate spacer which is also attached to the end of the long alkyl chain through an amide group. Loadings are in the vicinity of 30 μmole of nucleoside per gram of support. This functionalized material is commercially available.

Protected 3'-phosphoramidite deoxynucleosides are used to assemble the oligodeoxyribonucleotide. These are commercially available, but they can be prepared in the laboratory (McBride, L. J., and Caruthers, M. H., Tetrahedron Letters, 245 (1983), Dorper, T. and Winnacker, E. C., Nucleic Acids Res. 11, 2575 (1983), Atkinson, T. and Smith, M., in "Oligonucleotide Synthesis: A Practical Approach" (M. J. Gait ed.), p.35–81, IRL Press, Oxford, 1984), although this requires considerable chemical expertise. We currently use an Applied Biosystems Inc. Model 380A DNA Synthesizer for oligodeoxyribonucleotide synthesis. This instrument is capable of synthesizing three different oligodeoxyribonucleotides simultaneously. Syntheses are carried out on approximately 30 mg of solid support, containing 1 μmole of protected nucleoside. The coupling step uses 10 μmole of the appropriate nucleoside phosphoramidite in dry acetonitrile and 50 μmole of tetrazole in the same solvent. This coupling step is very moisture sensitive, due to the high reactivity of the protonated (by tetrazole) phosphoramidite, which will react very readily with water. Some of the large excess of phosphoramidite reacts with residual water, in order for the coupling reaction to take place efficiently. Coupling yields, using controlled pore glass as the solid support and diisopropyl phosphoramidites, are typically between 97% and 99%. Dry acetonitrile is conveniently prepared by drying HPLC grade material with activated 3A molecular sieves (Burfield et.al., J. Appl. Chem. Biotechnol. 28, 23 (1978)). If this is to be used on the instrument, it must be filtered through a 0.45 μm Teflon cartridge filter with a syringe in order to remove any fine particles present in the sieves.

Oligodeoxyribonucleotide chain assembly can also be carried out manually. A very detailed protocol for this manual procedure has been published recently (Atkinson and Smith, supra). A twelvefold excess of phosphoramidite is sufficient to ensure maximum coupling efficiency if (i) the reaction cell used is a small glass column, 1 cm in diameter and 3 cm long, fitted with a sintered glass disc of medium porosity (No. 3), a 3-way tap and a B14 quickfit top so that it can be stoppered and shaken, (ii) the solid support is washed thoroughly (5 times) with dry acetonitrile prior to the coupling step, this being filtered by using dry nitrogen pressure, drying the solid support thoroughly with dry nitrogen and leaving under nitrogen and, (iii) quickly adding the required amount of deoxynucleoside phosphoramidite in 0.4 ml of dry acetonitrile and the tetrazole solution in 0.6 ml of dry acetonitrile (transferred by using dry glass syringes, kept in a dessicator in between couplings).

Following chain assembly and removal of the phosphate methyl protecting groups with thiophenoxide ion, the oligodeoxyribonucleotide is cleaved from the solid support using concentrated ammonia solution. With the automated instrument the oligodeoxynucleotide solution is filtered from the solid support and is delivered to the collection vial in ammonia solution. Additional concentrated ammonia is then added (to 20 ml total volume in a 50 ml round-bottomed flask) to the crude oligodeoxyribonucleotide solution, the flask is sealed tightly and treated at 55° C. for 16 hours. After this reaction, the solution is evaporated to dryness and redissolved in 3 ml of sterile water.

The crude oligodeoxynucleotide can be purified by (i) reverse phase HPLC, (ii) strong anion exchange HPLC or (iii) polyacrylamide gel electrophoresis. In the case of reverse phase HPLC, use is made of the lipophilic nature of the dimethoxytrityl group. If the last 5'-dimethoxytrityl group is not removed, and the synthesis used an efficient capping reaction, then only the full length product should have this lipophilic group attached to it. This causes the desired product to be retarded on a reverse phase (μ-Bondapak $C_{18}$, 4.6 mm×25 cm) column, whereas the failure sequences elute with the void volume. In the case of a 30 mer for example, a buffer gradient is run from 20% to 30% acetonitrile (11 ml/min, in 0.1 M triethylammonium acetate, pH 7) over 20 minutes, and the product elutes at approximately 20 minutes. If further purification is desired, then the collected material is detrytylated for 20 minutes with 80% acetic acid and then rerun using the same buffer system, with a gradient of 0 to 30% acetonitrile over 15 minutes. In this case, the desired oligodeoxyribonucleotide elutes at 15 minutes. The collected material is then extensively dialyzed against water in Spectrapor 6 tubing, molecular weight cut-off 2000. Purification of 300 μl of a crude 30 mer in this manner usually gives approximately 1 to 2 $OD_{260}$ units of pure oligodeoxyribonucleotide. With longer sequences, the concentration of the organic phase is lowered in the initial run.

Purification by reverse phase HPLC is the method of choice for purifying oligodeoxyribonucleotide sequences up to approximately forty nucleotides in length. For longer sequences purification by polyacrylamide gel electrophoresis is preferred. In this procedure, 50 μl of the crude sample is mixed with 10 μl of formamide and loaded onto a 1.5 cm thick, 20 cm long gel. The sample wells are 1.5 cm×1.5 cm. The gels are in 7 M urea, 18% polyacrylamide being used for oligodeoxyribonucleotides up to twenty nucleotides long, 15% for twenty to thirty long and 10% for longer oligonucleotides. These gels are pre-electrophoresed for at least 1 hour prior to loading, and are run at 300 Volts. Dye tracks are run separately. The gel is electrophoresed for the maximum possible time in order to obtain the best resolution. Bromphenol blue generally runs at the level of an 11 to 13 mer and xylene cyanol at the level of a 60 mer. After electrophoresis, the gel is placed on a sheet of tlc silica gel (Merck DC-Plastikfolien Kieselgel 60 $F_{254}$, No. 5735) and irradiated with ultraviolet light (254 nm) whereupon the oligodeoxyribunucleotides appear as dark bands. The product band is usually the last major high molecular weight band. The appropriate gel slice is cut out, the product electroeluted, and then dialyzed as previously. Purification of 300 μl of a crude 30 mer by this procedure usually yields approximately 0.5 to 1.0 $OD_{260}$ units of pure oligodeoxyribonucleotide.

Strong anion exchange HPLC on Whatman Partisil 10SAX columns can also be used to purify synthetic oligodeoxyribonucleotides. In this case, separation is on the basis of charge and thus the product compound is usually the last peak to elute. Elution (for a 30 mer) is with a phosphate gradient (1 mM to 0.3 M) over 60 minutes in buffers containing 60% formamide. The method works well with oligodeoxyribonucleotides up to 30 to 40 mucleotides long (Scanlon et.al., J. Chromatography, 336, 189 (1984)). However, it is more time consuming than the reverse phase method and the ion exchange columns have a shorter life time. Nevertheless, it is the best method of assessing the degree of heterogeneity in the crude product mixture.

The sequence of the oligodeoxyribonucleotide can be confirmed, after 5'-end labelling with [γ-$^{32}$P] ATP, by a modified Maxam and Gilbert procedure (Maxam, A. M. and Gilbert, W., "Methods in Enzymology", 65, 499 (1980)). In this method, 60 μg of tRNA are used to precipitate 100 ng of labelled oligonucleotide, and the base specific reactions are carried out for 1 hour at 20° C.

End-Labelling of Oligodeoxyribonucleotides

We have observed that the use of a high pH, glycerol containing buffer system (Procedure 5A in Maxam and Gilbert Ref., supra) gives consistently high 5'-end labelling with $T_4$ polynucleotide kinase and [γ-$^{32}$P] ATP. The levels of labelling achieved using this procedure are much higher, usually by as much as ten times, than the levels achieved using the procedure normally recommended for the end labelling of oligodeoxyribonucleotides (Procedure 5B in Maxam and Gilbert Ref.). The labelling is normally carried out on 100 ng of oligodeoxyribonucleotide (corresponding to 10 μmole of a 30 mer), using 20 μmole of [γ-$^{32}$P] ATP and 20 units of $T_4$ polynucleotide kinase, for 1 hour. The labelled probe is then purified on a Sephadex G25 column (5×0.5 cm) precipitated in ethanol using 50 μg of tRNA to each fraction (8 drops each) containing the labelled product, dried under vacuum and diluted to 400 ng/ml in hybridization buffer with 40% (up to 42 mer) or 50% formamide. Hybridization buffer consists of 600 mM sodium chloride, 50 mM sodium phosphate pH 7.0, 5.0 mM EDTA, 0.02% ficoll, 0.02% bovine serum albumin, 0.02% polyvinyl pyrrolidone, 0.01% herring sperm DNA. The specific activity is approximately $9.0 \times 10^8$ cpm/μg. A small amount of the sample is checked for homogeneity by electrophoresis on a 10% polyacrylamide, 7 M urea gel.

Procedure for Hydridization Histochemistry (a) Preparation of Frozen Sections From Excised Tissues Freezing Tissue:

Moulds of heavy duty aluminium soil are prepared large enough to contain the tissue to be frozen, with at least 2 mm clearance. O.C.T. compound is added at 4° C. to just cover the base. A sample of fresh tissue up to 20 mm³ is positioned in the mould preferably within minutes of excision, orientation noted, and covered with O.C.T. Using forceps, the mould is lowered into a precooled bath of hexane containing dry ice. To prevent cracking of the tissue during freezing the surface of the O.C.T. is kept clear of the hexane to allow for expansion. For specimens larger than 20 mm³, it is preferable to first freeze the tissue on a copper plate lowered into the coolant on a metal gauze carrier with the surface to be sectioned upwards, then to invert the frozen specimen quickly into the mould, cover with a minimum of O.C.T. at 4° C. and re-freeze. Other liquid coolants may provide slightly superior morphology in 5–10 μm frozen sections, but generally more complex apparatus is required. Tissue prepared as described and sealed in plastic can be stored at −20° C. for up to 6 months with little loss of sectioning quality or of detectable mRNA. Inadequately sealed samples desiccate, especially at low temperatures, destroying morphology.

Sectioning:

Sections of 3–10 microns are cut in a cryostat at −10 to −20° C. and thawed on to dry glass slides, precoated with 1% gelatine hardened with 0.25% formaldehyde and kept at room temperature. The section on the slide is immediately frozen by placing on a dry ice block, and left for at least 5 minutes. This reduces ribonuclease activity and helps in adherence of the sections. Alternate sections retained for routine morphology and evaluation of X-ray film autoradiographs are left at room temperature until dry.

Fixation:

The slides are transferred from dry ice to freshly prepared glutaraldehyde fixative (4% glutaraldehyde, electron microscope grade, in 0.1M phosphate buffer pH 7.3 with 20% ethylene glycol) at 4° C., agitated and left for 5 minutes. Sections retained for routine morphology are fixed for 10 seconds in 10% formaldehyde in 75% ethanol, rinsed in water and stained or allowed to dry.

Pre-Hybridization:

Glutaraldehyde-fixed sections are rinsed at room temperature then at 40° C. in hybridization buffer, and left for 1 to 4 hours in fresh buffer to "pre-hybridize". To avoid the risk of rust contamination, glass or plastic slide racks and containers are recommended for this, and subsequent steps employing high salt solutions. Slides are rinsed in 2 changes of absolute ethanol at room temperature and left until dry. They can be stored over ethanol vapour, if necessary, for up to 1 week at 4° C. or 1 month at −20° C. with some risk of morphological deterioration at the lower temperature.

(b) Preparation of Sections from Freeze-dried Embedded Tissues

This procedure provides superior morphology in small tissue samples, especially of granule containing cells, due to retention of intracellular granules.

Freeze-drying Tissue:

Samples of fresh tissue not larger than 5 mm³ are frozen in liquid propane cooled by liquid nitrogen. Frozen samples are freeze-dried for 72 hours at −45° C. and $10^{-3}$ Torr with phosphorus pentoxide as desiccant. Whilst still under vacuum the temperature is raised at 3° C. per hour to 0° C., air is admitted and samples are removed to a vacuum desiccator containing dry silica gel and paraformaldehyde. Samples are then evacuated and left at 37° C. for 5 hours.

Embedding:

Tissue samples are removed directly to embedding moulds containing paraplast at 56° C. in a heated vacuum embedding chamber and evacuated for approximately half an hour or until bubbles no longer appear, indicating complete infiltration. Moulds containing tissues are removed to trays of ice and left until cooled, then stored at −20° C. for a limited period (not exceeding 2 months).

Sectioning:

Paraffin sections are cut at 2 to 10 $\mu$m on a conventional rotary microtome, transferred to distilled water at room temperature then onto slides pre-coated with 1% gelatine subsequently hardened with 0.25% formaldehyde. Each slide is warmed briefly if necessary to flatten and dry the section. The dry sections are then stored at −20° C. until ready to hybridize.

Pre-hybridization:

Sections are equilibrated to room temperature and soaked in xylene (2 changes of 3 minutes each) to remove paraffin, rinsed in absolute ethanol and allowed to dry. Immersion in hybridization buffer at 40° C., and subsequent procedures are as for frozen sections (see above).

Hybridization:

Before application of the probe stored sections are dried under vacuum at room temperature. The probe is boiled for 1 minute to separate strands, mixed and centrifuged. A volume of probe appropriate for the size of sections is applied to a coverslip (eg 20 $\mu$l for a 22×22 mm coverslip) and sections touched lightly on the drop until it spreads and the coverslip adheres by capillary action. Slides are laid on a raised plastic grill in a sealable chamber humidified by hybridization buffer. Rows of slides are covered with strips of thin plastic film, the chamber sealed and incubated for 1 to 3 days at a temperature determined by the probe length (see Table). 24 hours incubation is generally adequate, but as the hybridization signal does increase with time, and weekends may intervene, three days is a good standard.

Post-Hybridization Washing:

Slides are rinsed individually at room temperature in 4×SSC (standard saline-citrate solution, stock solution X20 is 3M sodium chloride, 0.3M sodium citrate in distilled water) until the coverslip falls off, then left immersed in 2×SSC until a batch is completed. 1 ×SSC is pre-warmed to a temperature determined by the probe length (see Table) and slides soaked for 30 minutes with frequent agitation. Approximately 200 ml of each solution for each 10 slides is recommended. Batches o%-slides are rinsed briefly in 2 changes of absolute ethanol with constant agitation and allowed to dry at room temperature.

TABLE

Hybridization and Washing Temperatures for Short Probes

| | 15 mer | 18 mer | 21 mer | 24 mer | 27 mer | 30 mer | >42 mer |
|---|---|---|---|---|---|---|---|
| Hybridization Temperature | R.T. | 30° C. | 30° C. | 30° C. | 40° C. | 40° C. | 40° C. |
| Washing[a] Temperature | 30° C. | 30° C. | 40° C. | 40° C. | 40° C. | 40° C. | 50° C. |

Probes 40 mer and less are in 40% formamide buffer, above 40 mer in 50% formamide buffer. This data was prepared using $^{32}$P labelled oligodeoxyribonucleotides corresponding to amino acids 111 to 115 and up to 124 of mouse glandular kallikrein[b] with 5 $\mu$m sections of mouse kidney and salivary glands as target tissues.

[a]The washing solution is 1XSSC.
[b]Richards et. al., J. Biol. Chem. 257, 2758 (1982).

Whole Animal Specimens

Whole small animal specimens are first frozen in hexane/dry ice or alternative solutions, then embedded in a mould of 2% carboxymethylcellulose gel, finely minced meat or other freeze-embedding compounds and re-immersed in hexane/dry ice until frozen.

Sections are cut at 20 to 60$\mu$ on an appropriate sledge cryomicrotore, e.g., P.M.V. at −20° C. The sections are collected by applying to the frozen tissue block a piece of adhesive tape which has been spread with a silicone adhesive, e.g., neutral cure silicone roof and gutter sealant (Dow Corning, Australia). After the section is cut it remains attached to the adhesive tape and is immediately fixed in 4% glutaraldehyde in 0.1M phosphate buffer pH 7.2 at room temperature, rinsed and pre-hybridized floating in dishes of hybridization buffer at 42° C. according to the protocol described above for tissue sections. After rinsing in ethanol, the tape is attached to a flat support, e.g., glass and subsequent hybridization and washing procedures are as for tissue sections. Alternatively, the section on tape can be hybridized and washed floating or immersed in the probe and washing solutions.

Tapes carrying sections are attached to a backing sheet in a light-proof cassette, covered with thin plastic film (e.g., "Gladwrap") and autoradiographed as described for tissue sections.

Autoradiography with $^{32}$P: (Detection of Hybridization Sites

Slides are taped to a backing sheet (blotting paper) in a film cassette leaving 1 to 2 mm gaps between and blank slides are laid at the edges of the group to ensure the film lies flat. Slides of different thicknesses should be in separate groups. As intensifying screens reduce resolution they are used only if very short exposures are necessary or on a second exposure of "negative" tissues. A sheet of the fastest available X-ray film (we use Kodak XAR5) is placed over the slides, a weight on the cassette and exposed for 12 to 24 hours at room temperature or at −80° C. if intensifying screens are used. The film is developed and fixed in Kodak liquid X-ray developer Type 2 and fixer. In evaluating the result comparison of the film with stained sections previously prepared, viewed on a transmitted light steromicroscope, may be helpful. A dark grey image after 24 hours exposure to XAR5 requires about 10 days exposure for G5 or 14 days for K5 liquid emulsion. There is little or no increase in numbers of developed silver grains beyond 21 days. A very light image on XAR5 is probably too weak a signal to expect adequate labelling in liquid emulsion autoradiographs but increased resolution can be obtained by the application of fine grain single emulsion coat X-ray film (Dupont—MRF 32) and a 1–4 week exposure. "Hotter" tissues can be treated similarly with a short exposure (1–2 days) prior to autoradiography with liquid emulsion. These images are useful for pinpointing labelled regions discernible only at high magnifications. Liquid emulsion autoradiography is then performed by essentially conventional techniques. Briefly, slides are dipped at 40° C. in G5 or K5 emulsion diluted 1:2 with distilled water, exposed at room temperature over silica gel, developed for 2 minutes in Kodak D19, rinsed in distilled water and fixed in Ilford Hypam diluted 1:4, all at 15° C. After a thorough rinse in distilled water tissues are stained by conventional procedures and mounted in D.P.X. (15% dibutyl phthalate and 10% Lustrex Pix 5 in xylene)

General Techniques

Tissue Preservation

Tissues may be frozen in a variety of ways including propane or iso-pentane cooled by liquid nitrogen, freon, liquid nitrogen slush or any means by which the tissue structure is not destroyed by ice crystals.

Alternatives to the use of fresh frozen tissues are tissues which have been chemically fixed using one or several of a number of agents commonly employed such as formaldehyde, glutaraldehyde, ethanol, acetic acid, picric acid, acrolein or the like which are introduced by perfusion or vapour or in which the tissue is immersed. The term "chemical fixation" here refers to any process which cross-links proteins, inactivates enzymes and/or precipitates nucleic acids.

Depending on the chemical agents employed it may be necessary to treat specimens with proteinases, e.g. proteinase K, prior to hybridization in order to render the tissue m-RNA or DNA accessible to the probe. An alterative to dissected or biopsy tissue specimens is the use of tissue, cell or organ cultures which are treated similarly to fresh tissue in that they are frozen and/or chemically fixed before hybridization. Further procedures do not necessarily include sectioning as this type of preparation is usually adhering to a solid or biological supporting material such as glass or agar or is in the form of a suspension. Cell suspensions can be first attached to glass or plastic or be taken through hybridization and washing procedures and attached to glass or plastic prior to autoradiography or viewing.

Sectioning of fixed or unfixed tissue above −10° C. is an alternative to frozen sectioning. Tissue may be embedded in a supporting medium such as gelatine, paraffin or plastic or the like and be cut on a rotary, sledge or ultramicrotome or may be cut on a vibratome or similar instrument without embedding or with minimal support (e.g., agar).

The hybridization temperature and formamide concentration of the hybridization buffer is varied according to the length of probe used, and the homology with tissue m-RNA sequences. The formamide concentration is varied in the range 0 to 60% and the temperature for hybridization can range from 20° C. to 70° C. The duration can be shortened to hours if the tissue m-RNA level, specific activity of probe and hybridization temperature are high enough.

The post-hybridization washing conditions are also varied according to probe length and homology with tissue mRNA. This step is essentially to remove excess probe and non-specific interactions. A balance of salt concentration, temperature and duration of wash is required where the homology of probe and tissue m-RNA sequences are uncertain. The hybridization and washing conditions for synthetic probes of varying lengths are described in the Table.

The following Examples illustrate the application of the techniques described in detail above to the determination of the presence and location of specific polynucleotide populations in various animal tissues in accordance with the present invention.

In Example 1 and Examples 3 to 7, oligonucleotides were synthesized complementary to mRNA sequences of regions cited and were end-labelled with $^{32}$PγdATP. The relevant method of tissue and section preparation is cited with each example. The hybridization of probe and section and subsequent procedures were performed according to the methods previously described.

EXAMPLE 1

A single-stranded kallikrein probe was prepared comprising a synthetic oligodeoxyribonucleotide 30 mer corresponding to amino acids 111–120 of mouse glandular kallikrein (Richards et al. J. Biol.Chem. 257(6), 2758–2761, 1982).

5' GGG CTT CAC AAC ATC TGT CAT GTC AGC AGG 3'

Figure 1B:
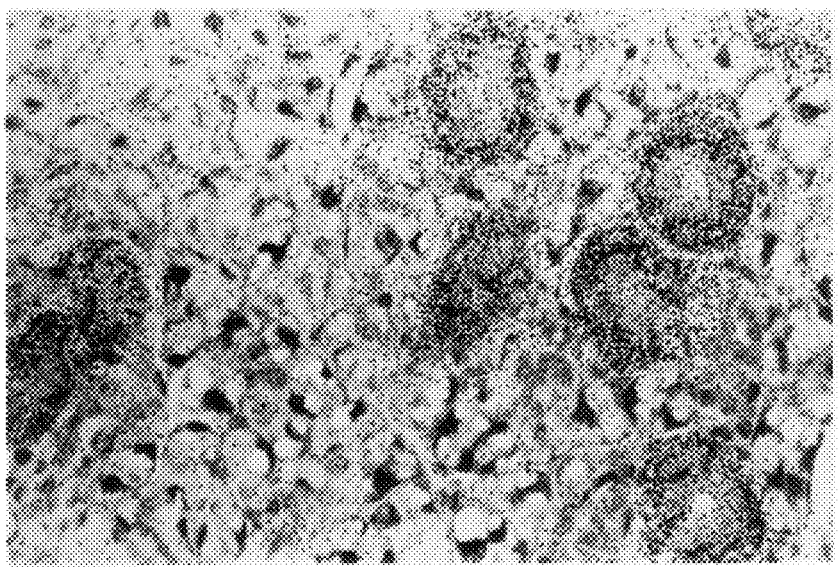
FIG. 1B is a liquid emulsion autoradiograph of a 3 µm paraffin section from a freeze-dried male mouse submandibular gland showing mRNA for kallikrein in cells of the granular convoluted tubules (Mag.×400).
Figure 1C:
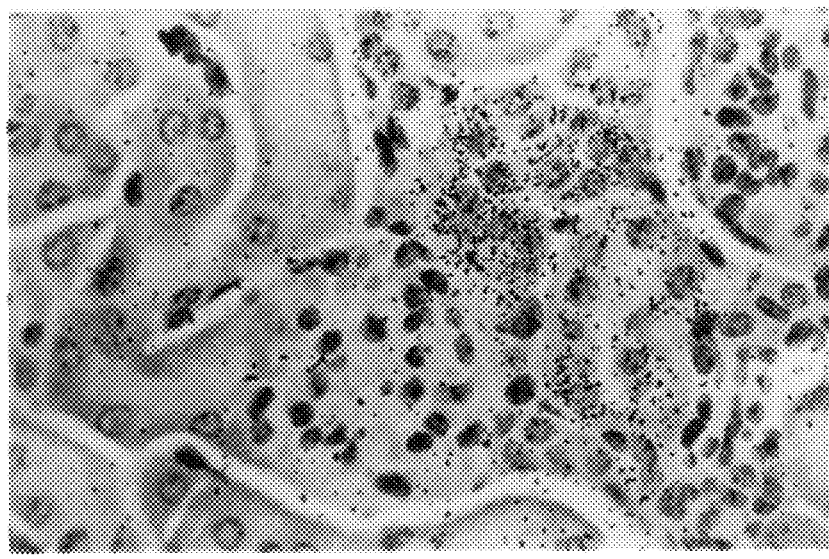
FIG. 1C is a liquid emulsion autoradiograph of a 3 µm paraffin section from a freeze-dried mouse kidney. The cortical area shows mRNA for kallikrein in cells of the distal convoluted tubule (Mag.×800).

This probe was then labelled and used to detect the location of mRNA for kallikrein in various tissues by the methods described above. FIG. 1A is an X-ray film autoradiograph from 40 μm section of whole male Swiss mouse showing mRNA for kallikrein to be present in kidney cortex and salivary glands (Mag.×2). FIG. 1B is a liquid emulsion autoradiograph of 3 μm paraffin section from a freeze-dried male mouse sub-mandibular gland showing mRNA for kallikrein to be located on cells of the granular convoluted tubules (Mag.×400). FIG. 1C is a liquid emulsion autoradiograph of 3 μm paraffin section from freeze-dried mouse kidney. This area of cortex shows mRNA for kallikrein to be present in cells of the distal convoluted tubule (Mag.×800).

EXAMPLE 2

The following example illustrates the synthesis of oligonucleotide probes involving DNA polymerase mediated "repair-synthesis" of synthetic substrates having a short section of complementary sequence at the 3' termini. Two oligodeoxynucleotide 30 mers were synthesized corresponding to the amino acid sequence region 104 to 113 and 111 to 120 as described by Richards et al, J. Biol. Chem., 257, 2758–2761, 1982. These oligonucleotides have a complementary sequence of 9 nucleotides at the 3' termini as shown.

5' ATG CTG CTC CGC CTC AGC AAG CCT GCT GAC 3'

3' GGA CGA CTG TAG TGT CTA CAA CAC TTC GGG 5'

The synthetic 30 mer (100 ng) were dissolved in 10 μl of 10 mM Tris buffer pH 7.5 with 1 mM EDTA, boiled or 5 minutes and cooled on ice for 1 minute. This solution was then added to the following mixture and reacted at 37° C.: $^{32}$Pα-dATP, 5 μl (50 μCi); 10 mM dGTP, dCTP, dTTP, 1 μl each; 10× medium buffer (500 mM sodium chloride; 10 mM Tris-HCl pH 7.5; 100 mM magnesium chloride; 10 mM dithiothreitol) 2.5 μl; E. coli DNA polymerase I (Klenow), 1 μl; distilled water, 3 μl. After 30 minutes the reaction was terminated by the addition of EDTA to give a final concentration of 12.5 mM and extracted with phenol-chloroform (1:1). The aqueous phase was passed through a 10×60 mm column of Sephadex G.25 (medium grade) equilibrated with 0.1M sodium chloride in 10 mM Tris pH 7.5, 1 ST EDTA buffer. The labelled probe which elutes at the void volume was precipitated with ethanol and redissolved in hydridization buffer and boiled prior to use.

Figure 2:
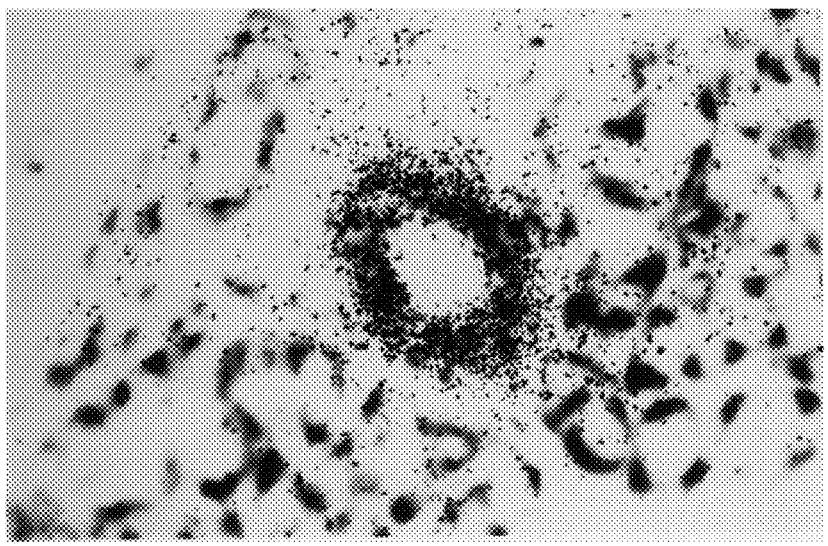
FIG. 2A is a liquid emulsion autoradiograph of a frozen section of a male mouse parotid gland after hybridization with a kallikrein probe prepared by the double strand approach described in Example 2. mRNA for kallikrein is located in the striated ducts of the parotid gland (Mag.×500).

FIG. 2A is a liquid emulsion autoradiograph of a frozen section showing male mouse parotid gland after hybridization with a kallikrein probe prepared by the double strand approach discribed above. mRNA for kallikrein is shown to be located in the striated ducts of the parotid gland (Mag.×500).

EXAMPLE 3

The following 30 mer oligonucleotide was synthesized to a region corresponding to amino acids 16 to 25 of mouse pre-pro epidermal growth factor (EGF) according to the sequence described by Scott et al, Science 221, 236–240, 1983.

5' GCT GAG TAT GCT AAT CTT TAA AAA CAC CAG 3'

Figure 3:
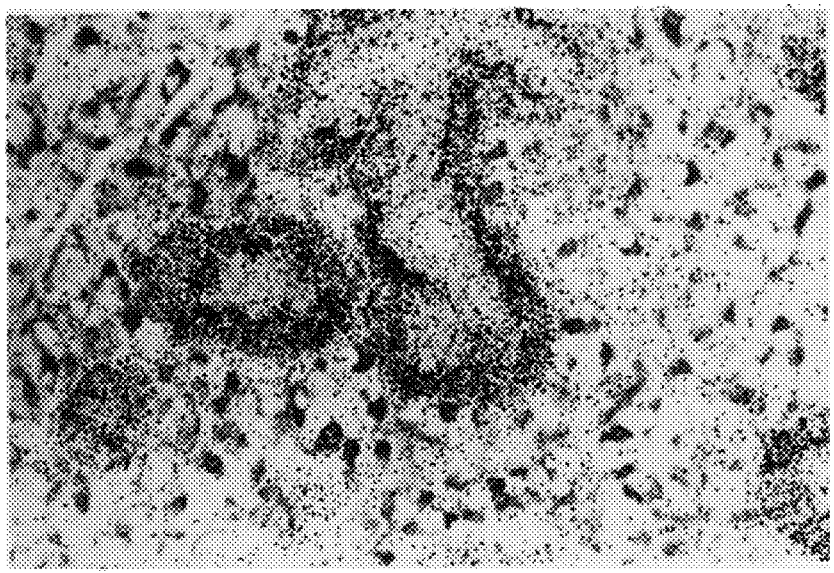
FIG. 3A is a 3 µm paraffin section of a freeze-dried salivary gland from a male Swiss mouse. mRNA for EGF is located in cells of the granular convoluted tubules of the submandibular gland (Mag.×400).

This probe was then labelled and used to detect the location of mRNA for EGF as previously described. FIG. 3A is a 3 μm paraffin section of a freeze-dried salivary gland from a male Swiss mouse. mRNA for EGF is shown to be located in cells of the granular convoluted tubules of the sub-mandibular gland (Mag.×400).

EXAMPLE 4

The following 24 mer oligonucleotide was synthesized corresponding to amino acids 9 to 16 of beta haemoglobin (adult), according to the sequence described by Kretschmer et al., J. Bio. Chem. 256, 1975–1982, 1981. This sequence region was chosen to have maximum sequence difference to gamma haemoglobin (fetal).

5' CTT GCC CCA GAA GCC GGT GAC GGC 3'

Figure 4:
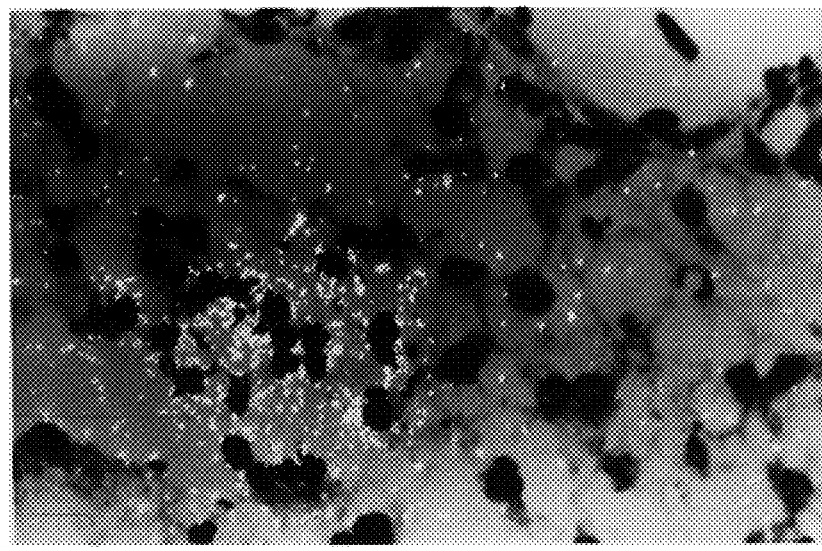
FIG. 4A is an autoradiograph of a 5 μm frozen section photographed by polarized incident light showing silver grains white against a dark background. Labelled are erythropoietic cells within the liver of a fetal sheep at 142 days of gestation, showing that mRNA for beta (adult) haemoglobin is present (Mag.×1000).

After labelling, this probe was used to detect the location of mRNA for beta (adult) haemoglobin. FIG. 4(a) is an autoradiograph of 5 μm frozen section photographed by polarized incident light showing silver graphs white against a dark background. Labelled are erythropoietic cells within the liver of a fetal sheep at 142 days of gestation, showing that mRNA for beta (adult) haemoglobin is present. (Mag.×1000).

EXAMPLE 5

The following 40 mer oligonucleotide was synthesized corresponding to amino acids 19 to 32 of human calcitonin according to the sequence described by Craig et al. Nature 295, 345–347, 1982.

5' AGG TGC TCC AAC CCC AAT TGC AGT BCG GCG GAA CGT GTG A 3'.

Figure 5:
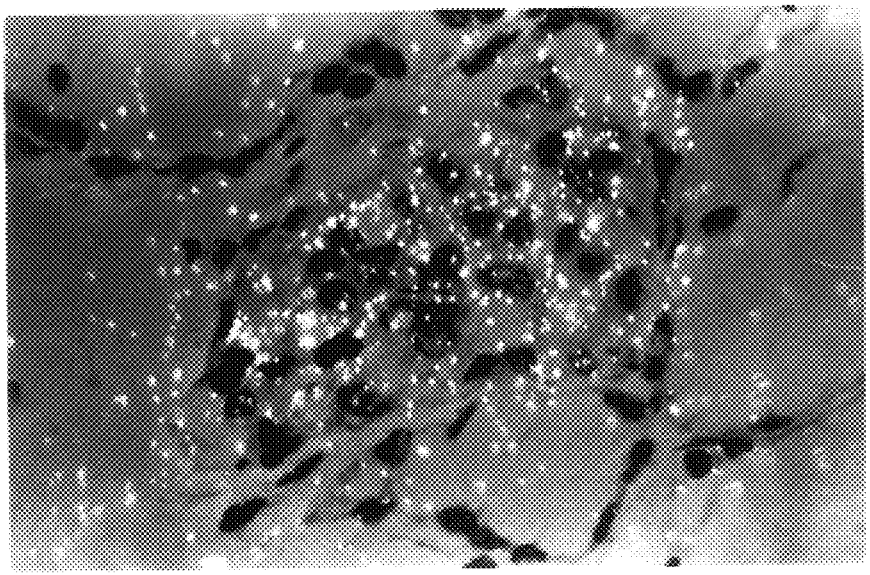
FIG. 5A is an autoradiograph photographed by polarized incident light. A 5 μm frozen section of a human medullary thyroid carcinoma shows calcitonin mRNA in proliferating C-cells located between follicles (Mag.×1000).

After labelling, this synthetic probe was used to detect the location of calcitonin mRNA by the methods previously described. FIG. 5A is an autoradiograph photographed by polarized incident light. A 5 μm frozen section of human medullary thyroid carcinoma showing calcitonin mRNA to be present in proliferating C-cells located between thyroid follicles. (Mag.×1000).

EXAMPLE 6

The following 39 mer oligonucleotide was synthesized corresponding to amino acids −1 to +12 of bovine prepro-AVP-neurophysin according to the sequence described by Land et al. Nature 302, 342–344, 1983.

5' CCT CTT GCC GCC CCT TGG GCA GTT CTG GAA GTA GCA ACC 3'

Figure 6:
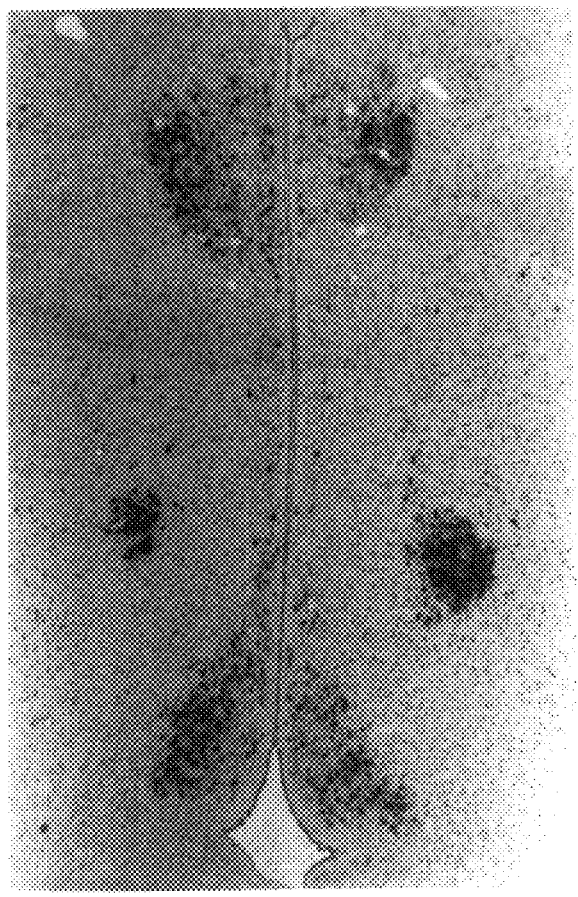
FIG. 6A is an autoradiograph of a 10 μm frozen section from sheep hypothalamus. The probe hybridized with mRNA in neurons of the paraventricular nucleus (Mag.×40).

This probe was labelled and used to locate mRNA by the methods previously described. FIG. 6A is an autoradiograph of 10 μm frozen section from sheep hypothalamus. The probe has hybridized with mRNA in neurones of the paraventricular nucleus. (Mag.×40).

EXAMPLE 7

Separate 30 mer oligonucleotides were synthesized corresponding to amino acids 125 to 134 of bovine oxytocin-neurophysin I [Probe A—example 7(a)] and AVP-neurophysin II [Probe B—example 7(b)] according to sequences described by Land et al. Nature 302, 342–344, 1983.

Probe A 5' ATT GTC ATA ATT CCT AGG GAT GAT TAC AGA 3'

Probe B 5' CCC CGC CAG CTG CAC CAG CCG CAG CAA CAA 3'

Figure 7A:
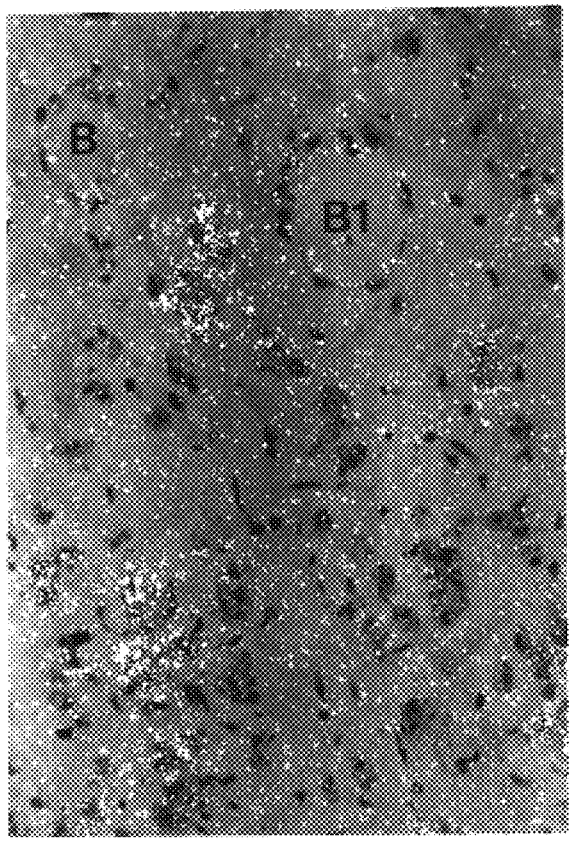
FIG. 7A is an autoradiograph of a 10 μm frozen section of hypothalamus from a lactating ewe. Separate 30-mer oligonucleotides corresponding to amino acids 125–134 of bovine oxytocin—neurophysin I were used as probes (Mag.×300).
Figure 7B:
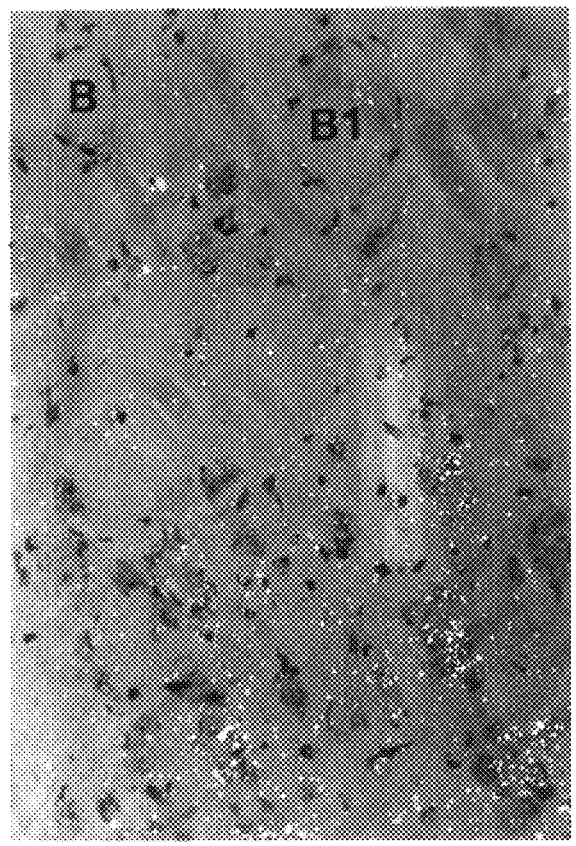
FIG. 7B is an autoradiograph of a 10 μm frozen section of hypothalamus from a lactating ewe. Separate 30-mer oligonucleotides corresponding to amino acids 125–134 of bovine oxytocin—AVP neurophysin II were used as probes (Mag.×300).

This is a region of maximum difference in nucleotide sequence for these two hormones and in this example each probe was labelled and applied to an adjacent 10 μm frozen section of hypothalamus from a lactating ewe. Blood vessels and neurones common to both sections are evident in FIGS. 7A and 7B. Using blood vessels B and B1 as landmarks it is evident that mRNA's for the hormones oxytocin (a) and AVP (b) are present in different neurones. (Mag.×300).

EXAMPLE 8

This example illustrates the standard components of a diagnostic kit for hybridization histochemistry in accordance with the present invention.

A. Reagents included in kit:

Salts for hybridization buffer to be reconstituted in 150 ml distilled water.

Deionized formamide −100 ml 200 ng labelled synthetic oligonucleotide probe as dry pellet containing 200 μg t-RNA—to be reconstituted in 400 μl hybridization buffer.

200 ng labelled synthetic oligonucleotide probe as above but of the complementary DNA sequence to the probe of interest to act as a negative control.

Salts for 4×SSC—to be reconstituted in 250 ml distilled water.

Salts for 2×SSC—to be reconstituted in 250 ml distilled water.

Salts for 1×SSC—to be reconstituted in 250 ml distilled water.

Instruction sheet including method for tissue preparation, sectioning, fixation, pre-hybridization, hybridization, post-hybridization washing, X-ray film and liquid emulsion autoradiography.

B. Formulae:

(i) Hybridization Buffer

600 EM sodium chloride; 50 μm sodium phosphate pH 7.0; 5.0 mM E.D.T.A.; 0.02% (w/v) ficoll; 0.02% (w/v) bovine serum albumin; 0.02% (w/v) polyvinyl pyrrolidone; 0.1% (w/v) leming sperm DNA; 40% (w/v) formamide (deionized).

(ii) Standard Saline-Citrate (SSC)

1×SSC is 0.15 M NaCl; 0.015 M sodium citrate.

What is claimed is:

1. A hybridization method for determining the presence and location in a population of animal or plant cells of a specific target polynucleotide population which comprises:

(a) preparing a sample of cells from the population to be examined;

(b) hybridizing the sample of cells with a substantially pure chemically synthesized labelled single-stranded oligonucleotide probe, wherein said probe is complementary to a representative portion of the target polynucleotide, wherein the probe is from 10 to 100 nucleotides, and (c) detecting or identifying the locations in the sample of cells where labelling by hybridization of the labelled probe has occurred, so as to determine the presence and location in a population of animal or plant cells of a specific target nucleotide population.

2. The method according to claim 1, wherein any unhybridized probe is removed from the sample of cells prior to detection of labelling.

3. The method according to claim 1, wherein the sample of cells is in the form of a suspension.

4. The method according to claim 1, wherein the synthetic, oligonucleotide probe is from 20 to 40 nucleotides.

5. The method according to claim 1, wherein said polynucleotide is selected from the group consisting of mRNA, pre-mRNA, viral RNA and viral DNA.

* * * * *